US007941282B2

(12) United States Patent
Ziegel et al.

(10) Patent No.: US 7,941,282 B2
(45) Date of Patent: May 10, 2011

(54) ESTIMATING WORST CASE CORROSION IN A PIPELINE

(75) Inventors: Eric R Ziegel, Houston, TX (US); Richard S. Bailey, Ashtead (GB); Kip P. Sprague, Anchorage, AK (US)

(73) Assignees: BP Exploration Operating Company Limited, Sunbury-on-Thames (GB); BP Corporation North America Inc., Houston, TX (US)

( * ) Notice: Subject to any disclaimer, the term of this patent is extended or adjusted under 35 U.S.C. 154(b) by 85 days.

(21) Appl. No.: 12/349,851

(22) Filed: Jan. 7, 2009

(65) Prior Publication Data
US 2010/0030491 A1    Feb. 4, 2010

Related U.S. Application Data

(60) Provisional application No. 61/085,692, filed on Aug. 1, 2008.

(51) Int. Cl.
  *G01B 3/52* (2006.01)
  *G01B 5/02* (2006.01)
(52) U.S. Cl. .............................. 702/34; 702/35; 702/170
(58) Field of Classification Search ................... 702/12, 702/34, 35, 170, 179; 73/602; 376/249; 716/4; 703/7, 9
  See application file for complete search history.

(56) References Cited

U.S. PATENT DOCUMENTS

| | | | |
|---|---|---|---|
| 4,935,195 A | 6/1990 | Palusamy et al. | |
| 4,998,208 A | 3/1991 | Buhrow et al. | |
| 5,072,388 A | 12/1991 | O'Sullivan et al. | |
| 5,965,818 A | 10/1999 | Wang | |
| 6,487,518 B1 | 11/2002 | Miyazaki et al. | |
| 6,556,924 B1 | 4/2003 | Kariyawasam et al. | |
| 6,813,949 B2 | 11/2004 | Masaniello et al. | |
| 7,013,249 B1 | 3/2006 | Davis | |
| 7,035,777 B2 | 4/2006 | Araki et al. | |
| 7,263,887 B2 | 9/2007 | Sfeir et al. | |

(Continued)

FOREIGN PATENT DOCUMENTS

CA         2435626 A1    1/2005
(Continued)

OTHER PUBLICATIONS

Vose, Risk Analysis, 2d. ed., (Wiley, 2000), Chapter 4.

(Continued)

*Primary Examiner* — John H Le
(74) *Attorney, Agent, or Firm* — Rodney M. Anderson

(57) ABSTRACT

A method and system for estimating the worst case corrosion in a pipeline for which pipeline wall thickness measurements are limited to sampled ultrasonic or radiography (UT/RT) measurements. A data library contains distributions of in-line inspection (IL) measurements for other pipelines, calibrated to correspond to UT/RT measurements as needed. These ILI datasets are randomly sampled multiple times, to obtain multiple sample sets from each ILI dataset. Candidate statistical distributions are evaluated for each sample set to determine which of the candidate statistical distributions most accurately estimates the worst case corrosion measured by ILI. A discriminant function is then derived from sample statistics and pipeline descriptors associated with the sample sets, along with the best candidate statistical distribution for that sample set. Sample statistics and pipeline descriptors for the pipeline with sampled UT/RT measurements are then applied to the discriminant function to determine the best one of the candidate statistical distributions for extreme value estimation, and the worst case corrosion is then determined using that best statistical distribution.

24 Claims, 7 Drawing Sheets

U.S. PATENT DOCUMENTS

| | | | |
|---|---|---|---|
| 2005/0149305 | A1 | 7/2005 | Araki et al. |
| 2006/0229855 | A1 | 10/2006 | Araki et al. |
| 2006/0283251 | A1 | 12/2006 | Hunaidi et al. |
| 2006/0288756 | A1 | 12/2006 | De Meurechy |
| 2009/0326865 | A1* | 12/2009 | Ziegel et al. .................. 702/179 |

FOREIGN PATENT DOCUMENTS

| | | |
|---|---|---|
| CN | 101071098 A | 11/2007 |
| WO | 2008/016697 A2 | 2/2008 |

OTHER PUBLICATIONS

Fougeres et al., "Pitting Corrosion: Comparison of Treatments with Extreme-Value-Distributed Responses", Technometrics, vol. 48, No. 2 (American Statistical Association; American Society for Quality, 2006).

Isogai et al., "Models and Inference for Corrosion Pit Depth Data", Extremes, vol. 7 (Springer Science+Business Media, Inc., 2004), pp. 253-270.

Martinsek, "Sequential Estimation of the Maximum in a Model for Corrosion Data", Ann. Inst. Statist. Math., vol. 52, No. 4 (2000), pp. 646-657.

Scarf et al., "Estimation of extremes in corrosion engineering", J. Appl. Statistics, vol. 23, No. 6 (Carfax Publishing Co., 1996), pp. 621-643.

TWI Limited, "Guidelines for use of statistics for analysis of sample inspection and corrosion", Research Report 016 (Crown copyright, 2002).

Irquidi-Macdonald et al., "Performance Comparison Between a Statistical Model, a Deterministic Model, and an Artificial Neural Network Model for Predicting Damage From Pitting Corrosion", J. Res. Natl. Inst. Stand. Technol., vol. 99, No. 4 (NIST, 1994), pp. 495-504.

Meeker et al., Statistical Methods for Reliability Data (Wiley, 1997), pp. 82-89.

Venables et al., Modern Applied Statistics with S, 4th ed. (Springer, 2003), pp. 331-341.

Hawn, "Extreme Value Prediction of Maximum Pits on Pipelines", Materials Performance (1977), pp. 29-32.

Bolzoni et al. "Application of probabilistic models to localized corrosion study," La Metallurgia Italiana 98 (2006), pp. 9-15. (English Abstract at end of article).

Caleyo et al. "A reliability-based approach for the condition assessment of corroding pipelines," J. Pipeline Integrity 2 (2003), pp. 143-157.

Rivas et al. "Extreme value analysis applied to pitting corrosion experiments in low carbon steel: Comparison of block maxima and peak over threshold approaches," Corrosion Science 50, 2008-Elsevier, pp. 3193-3204.

Velaquez et al. "Pitting corrosion models improve integrity management, reliability," Oil and Gas Journal (Jul. 27, 2009), pp. 56-58, 60, and 62.

Afifi et al., Computer-Aided Multivariate Analysis, 4th Ed. (Chapman&Hall/CRC, Boca Raton, 2004), Chapter 11, pp. 249-279.

\* cited by examiner

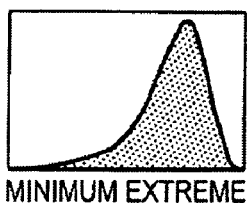
FIG. 5A
MINIMUM EXTREME
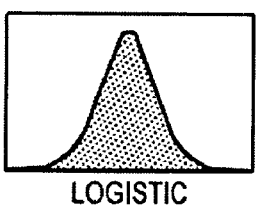
FIG. 5B
LOGISTIC
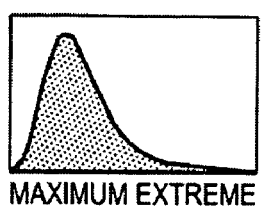
FIG. 5C
MAXIMUM EXTREME
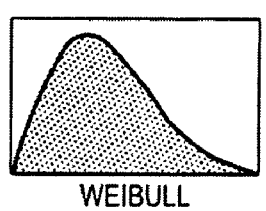
FIG. 5D
WEIBULL
FIG. 5E
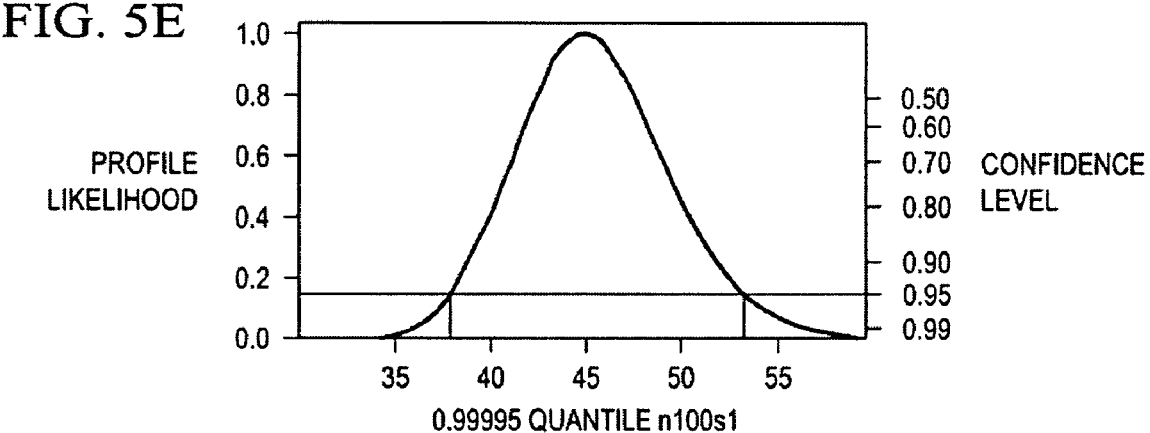
FIG. 5F
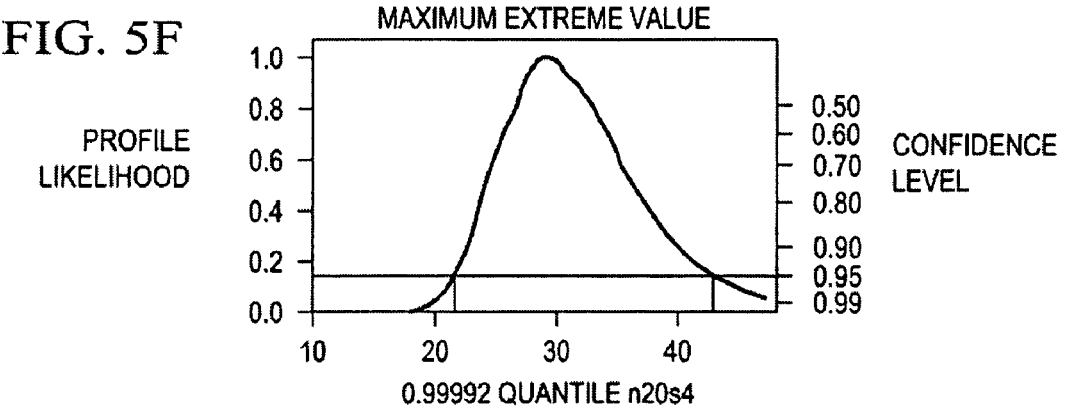

ESTIMATING WORST CASE CORROSION IN A PIPELINE

CROSS-REFERENCE TO RELATED APPLICATIONS

This application claims priority, under 35 U.S.C. §119(e), of Provisional Application No. 61/085,692,. filed Aug. 1, 2008, which is fully incorporated herein by this reference.

STATEMENT REGARDING FEDERALLY SPONSORED RESEARCH OR DEVELOPMENT

Not applicable.

BACKGROUND OF THE INVENTION

This invention is in the field of pipeline inspection. In one of its aspects, the invention is directed to the evaluation of the worst case corrosion in a pipeline from sampled measurements.

Maintaining the integrity of pipelines is a fundamental function in maintaining the economic success and minimizing the environmental impact of modern oil and gas production fields and systems. In addition, pipeline integrity is also of concern in other applications, including factory piping systems, municipal water and sewer systems, and the like. Similar concerns exist in the context of other applications, such as production casing of oil and gas wells. As is well known in the field of pipeline maintenance, corrosion and ablation of pipeline material, from the fluids flowing through the pipeline, will reduce the thickness of pipeline walls over time. In order to prevent pipeline failure, it is of course important to monitor the extent to which pipeline wall thickness has been reduced, so that timely repairs or replacement can be made.

The direct physical measurement of pipeline wall thickness is not practical because of the necessarily destructive nature of such measurement. Accordingly, various indirect pipeline wall thickness measurement techniques have been developed over the years. The most widely used measurement technologies acquire measurements of thickness at selected locations along a producing pipeline, such locations either randomly selected or specifically selected based on models or other assumptions of the most vulnerable locations to loss of wall thickness. These measurement technologies include ultrasonic measurement, and imaging by way of x-rays or radiography (RT), each of which examine pipeline walls from the exterior at specific locations (e.g., over a one foot section). However, the exterior of the pipeline must be directly accessed to obtain measurements according to these technologies. In extreme environments, this exterior access can require removal and replacement of thermal insulation, for example. To the extent that portions of the pipelines are underground, RT and ultrasonic tomography (UT) measurements are either not done, or require excavation. As such, it is not practical to acquire RT and UT measurements at small intervals along the entire length of a pipeline. Rather, for these and other reasons, these measurement technologies are typically carried out by random or semi-random sampling of wall thickness along the pipeline.

In the context of pipeline integrity, the extreme value of minimum wall thickness (or, conversely, maximum wall thickness loss) is of concern. Because corrosion is the leading cause of wall thickness loss of pipelines, in practice, this minimum wall thickness value is often referred to as the "worst case corrosion". Accordingly, sampled measurement approaches are useful only to the extent that the sample measurements lend insight into the extreme minimum value. Fundamental statistical theory can provide such insight, under the assumption that the population of wall thickness measurements along the entire length of the pipeline (e.g., a measurement taken in each one-foot section along the pipeline length) follows a known statistical distribution. In other words, assuming a statistical distribution of wall thicknesses along the length of the pipeline, a reasonable sample size of measurements can then provide an indication of the maximum wall thickness loss to a certain confidence level. Unfortunately, it has been observed that measurements of wall thickness along the length of an actual pipeline do not typically follow a well-behaved statistical distribution. Worse yet, it has been observed that wall thickness measurement distributions vary widely from pipeline to pipeline. As a result, it is difficult to characterize the extreme value of worst case corrosion along a pipeline from these sampled measurements of pipeline thickness, to any reasonable confidence level.

Another pipeline wall thickness measurement technology is referred to as "in-line inspection" (ILI). According to this technology, a vehicle commonly referred to as a "pig" travels in the interior of the pipeline along its length, propelled by the production fluid itself or otherwise towed through the pipeline. The pig includes transducers that indirectly measure the wall thickness of the pipeline repeatedly along the pipeline length as the pig travels. Measurement technologies used in ILI include magnetic flux leakage techniques that measure the extent to which a magnetic field can be induced into the pipeline wall, from which the wall thickness can be inferred. ILI inspection can also be carried out using ultrasonic energy, as well-known in the art. As such, ILI can acquire measurements of wall thickness at small intervals along the entire length of a pipeline. Unfortunately, ILI monitoring cannot be applied to all pipelines, because of factors such as construction, location, or geometry.

By way of further background, it is known to characterize pipeline integrity by applying sample thickness measurements to a predictive model of the pipeline. Known predictive models apply parameters such as properties of the fluid carried by the pipeline, pressure, temperature, flow rate, and the like, such that a minimum wall thickness can be calculated given sample measurements of the wall thickness. The accuracy of such computer simulations in characterizing the minimum wall thickness of course depends on the accuracy with which the model corresponds to the true behavior of the pipeline. And, in turn, the accuracy of the model depends on the accuracy of the assumptions underlying the model to the actual pipeline. But in practice, real-world pipelines vary widely from one another in corrosion behavior, due to structural and environmental variations that are not contemplated by the model or its underlying assumptions. As more complicated models are formulated to include the effects of these variations, the resulting computations will of course also become more complicated.

By way of further background, it is known to evaluate equipment reliability by selecting a statistical distribution, and applying Monte Carlo simulations to that statistical distribution, to plan a reliability evaluation.

By way of further background, our copending U.S. patent application Ser. No. 12/164,971, filed Jun. 30, 2008, entitled "Rapid Data-Based Adequacy Procedure for Pipeline Integrity Assessment", fully incorporated herein by this reference, discloses a method and system for evaluating the sample coverage of ultrasonic or radiography (UT/RT) measurements of pipeline wall thickness for statistical validity. This approach uses a data library of distributions of in-line inspection (ILI) measurements for some pipelines, and generates statistics from random sample simulation of those distributions at various sample coverages. The sampled UT/RT measurements from another pipeline are used to identify one or more ILI-measured pipeline datasets to which it is most similar. The statistics from the simulations of those most similar pipeline datasets are then used to determine whether the sample coverage of the UT/RT measurements is sufficient to draw desired conclusions about the extreme value of wall loss in the sampled pipeline.

BRIEF SUMMARY OF THE INVENTION

It is therefore an object of this invention to provide a method and system to accurately characterize a worst case value of pipeline wall thickness loss ("worst case corrosion") along a pipeline based on sample measurements of wall thickness.

It is a further object of this invention to provide such a method and system that provides improved confidence in sampled pipeline wall thickness measurements.

It is a further object of this invention to provide such a method and system that improves the efficiency of pipeline wall thickness measurement resources.

It is a further object of this invention to provide such a method and system that can determine worst case wall thickness loss through a computer algorithm that can be executed rapidly for a large number of pipelines.

It is a further object of this invention to provide such a method and system that can determine the worst case corrosion by utilizing available information on pipeline corrosion distributions that have been characterized by a 100% inspection process for pipelines, such as in-line inspection (ILI).

Other objects and advantages of this invention will be apparent to those of ordinary skill in the art having reference to the following specification together with its drawings.

The present invention may be implemented into a computerized method, an evaluation system programmed to perform the method, and a computer program stored in a computer readable medium, by way of which an extreme value of pipeline wall thickness loss can be determined from sample measurements. A library of measurement datasets acquired by a 100% inspection method, such as in-line inspection, for a subset of the pipelines is stored in a database. In an aspect of the invention, simulated sampling of these datasets is used to derive a discrimination function or equation set, by way of which a statistical distribution shape can be selected from sample statistics and other pipeline descriptors. Sampled wall thickness loss measurements from another pipeline are statistically characterized, and the sample statistics and other pipeline descriptors are applied to the discrimination function to select a statistical distribution shape for the sample set. The extreme value of maximum wall thickness loss is then determined from the selected statistical distribution shape, as fit to the sampled wall thickness loss measurements for the sampled pipeline.

BRIEF DESCRIPTION OF THE SEVERAL VIEWS OF THE DRAWING

FIGS. 5a through 5d are plots illustrating the shape of examples of candidate statistical distributions, used in an example of an embodiment of the invention.

FIG. 5e illustrates an example of the evaluation of an extreme value quantile according to an embodiment of the invention.

FIGS. 5f through 5i are plots illustrating the evaluation of extreme value quantiles of candidate statistical distributions according to an embodiment of the invention.

DETAILED DESCRIPTION OF THE INVENTION

The present invention will be described in connection with its embodiments, including its preferred embodiment, in connection with a method and system for monitoring and evaluating pipeline integrity in a production field and system for oil and gas. However, it is contemplated that this invention can also provide important benefit in other applications, including, for example, the monitoring and evaluating of production casing integrity in oil and gas wells, and the monitoring and evaluating of pipeline integrity in other applications such as water and sewer systems, natural gas distribution systems on the customer side, and factory piping systems, to name a few. Accordingly, it is to be understood that the following description is provided by way of example only, and is not intended to limit the true scope of this invention as claimed.

Figure 1:
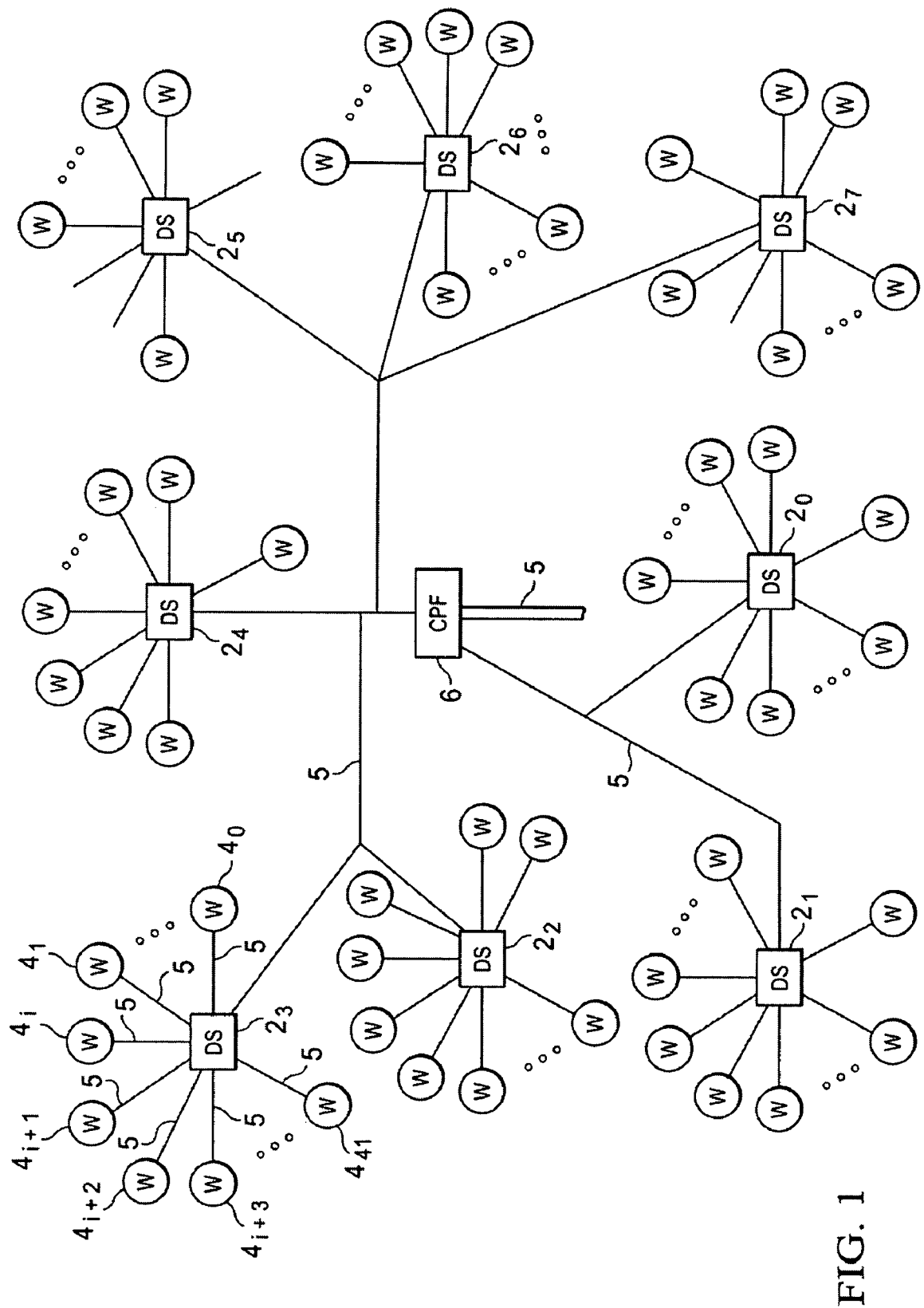
FIG. 1 is a schematic diagram of an example of a production field in connection with which the preferred embodiment of the invention may be used.

Referring first to FIG. 1, an example of an oil and gas production field, including surface facilities, in connection with which an embodiment of the invention may be utilized, is illustrated in a simplified block form. In this example, the production field includes many wells W, deployed at various locations within the field, from which oil and gas products are to be produced in the conventional manner. While a number of wells W are illustrated in FIG. 1, it is contemplated that modern production fields in connection with which the present invention may be utilized will include many more wells than those wells W depicted in FIG. 1. In this example, each well W is connected to an associated one of multiple drill sites 2 in its locale by way of a pipeline 5. By way of example, eight drill sites $2_0$ through $2_7$ are illustrated in FIG. 1; it is, of course, understood by those in the art that many more than eight drill sites 2 may be deployed within a production field. Each drill site 2 may support many wells W; for example drill site $2_3$ is illustrated in FIG. 1 as supporting forty-two wells $4_0$ through $4_{41}$. Each drill site 2 gathers the output from its associated wells W, and forwards the gathered output to processing facility 6 via one of pipelines 5. Eventually, processing facility 6 is coupled into an output pipeline 5, which in turn may couple into a larger-scale pipeline facility along with other processing facilities 6.

In real-world oil production, the pipeline system partially shown in FIG. 1 would connect into a larger pipeline system, along with many other wells W, drilling sites 2, pipelines 5, and processing facilities 6. Some pipeline systems include thousands of individual pipelines that are interconnected into an overall production and processing system. As such, the pipeline system illustrated in FIG. 1 can represent a miniscule portion of an overall production pipeline system.

While not suggested by the schematic diagram of FIG. 1, in actuality pipelines 5 vary widely from one another in construction and geometry, in parameters including diameter, nominal wall thickness, pipeline age, pipeline type, overall length, numbers and angles of elbows and curvature, location (underground, above-ground, underwater, or extent of such placement), to name a few. In addition, parameters regarding the contents (i.e., liquids, gases, solids such as sand, scale, or others, or combinations of these fluids and solids) carried by the various pipelines 5 also can vary widely in composition, pressure, temperature, flow rate, and the like. As known in the art, these variations among pipeline construction, geometry, contents, and nominal operating condition affect the extent and nature of corrosion and ablation of the pipeline walls. In addition, it has been observed, in connection with this invention, that the distribution of wall loss (i.e., wall thickness loss) measurements along pipeline length also varies widely among pipelines in an overall production field, with no readily discernible causal pattern relative to construction or fluid parameters.

As mentioned above, some pipelines in a production pipeline system such as that illustrated in part in FIG. 1 can be fully inspected, from the standpoint of pipeline wall thickness, along their entire length by way of in-line inspection (ILI). As known in the art, ILI involves the insertion of a measurement tool, such as the tool commonly referred to as a "pig", into the pipeline. Conventional measurement pigs are generally cylindrical bodies that include navigational or positional systems to monitor the location of the pig in the pipeline, along with instrumentation for measuring pipeline wall thickness as the pig travels along the pipeline propelled by the production fluid. Alternatively, the pig may be towed along the pipeline, if the pipeline is being measured while shutdown. Conventional measurement devices such as ILI pigs measure loss of pipeline wall thickness using the technologies of magnetic flux leakage (MFL), ultrasonic tomography, electrostatic induction and the like. Examples of conventional ILI pigs suitable for obtaining ILI measurements include the CPIG MFLCAL ILI instruments available from Baker Hughes Pipeline Management Group, and the HIRES metal loss mapping tools available from Rosen Inspection Technologies; other types of measurement devices and mapping tools known by those skilled in the art are also suitable for use in connection with this embodiment of the invention.

As known in the art, and as mentioned above, a sizeable number of pipelines 5 in a large-scale pipeline system are "unpiggable" (unpassable by pigs, or otherwise inaccessible to in-line inspection), in that those pipelines cannot be inspected by way of ILI for one or more various reasons. For example, access to the pipeline may be restricted, valves or other impassable fittings may impede the travel of a pig through the pipeline, or a given pipeline may have varying diameter along its length such that a pig cannot snugly engage the pipeline walls as it travels. However, the operator of the production field must also monitor these unpiggable pipelines for loss of wall thickness. As discussed above, the monitoring of these unpiggable pipelines 5 is performed by sample measurements taken externally along the length of the pipeline, using conventional methods such as ultrasonic tomography (UT) and radiography (RT); other conventional measurement technologies are also suitable for use in connection with embodiments of the invention. In this example, conventional UT/RT measurements are typically obtained as the average of wall thickness measurements over some incremental distance (e.g., one foot) along the length of the pipeline. Conventional sampled UT/RT wall thickness measurements involve a substantial amount of labor, such as removing insulation or coatings from the pipeline; and physically traveling between sample locations. As such, sampled UT/RT wall thickness measurements are typically performed on a periodic scheduled basis, especially in large-scale pipeline systems. For pipeline systems in a hostile climate, such pipeline wall thickness measurements may only be available in certain months in the year, because some locations along some pipelines may require special precautions to be safely accessible in certain seasons.

The goal of pipeline integrity monitoring is to determine the maximum pipeline wall loss along a given pipeline to enable timely maintenance operations. It has been observed that corrosion is generally the cause of loss of early pipeline wall thickness loss in actual pipeline systems. As such, maximum wall thickness loss is often referred to in the art, and will be referred to in this specification, as "worst case corrosion", even though the particular physical mechanism (corrosion, ablation, etc.) by which pipeline walls are reduced in thickness is not of importance in connection with this invention. Embodiments of this invention are directed to providing a statistically sound estimate of worst case corrosion in pipelines from which only sampled measurements have been acquired, based on the statistical behavior of those pipelines for which ILI measurements along their entire length have been obtained.

Figure 2:
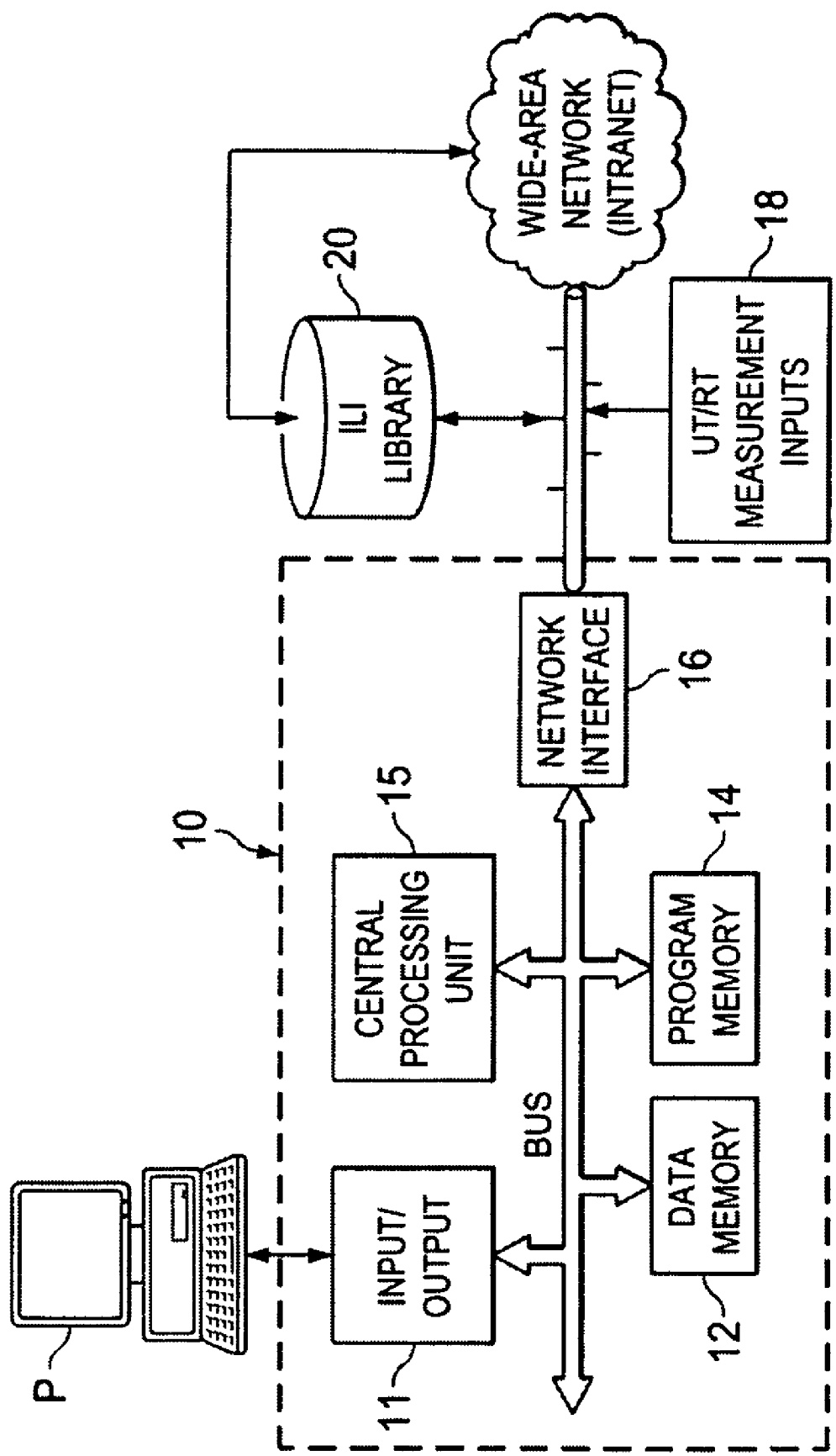
FIG. 2 is an electrical diagram, in block form, of an evaluation system programmed to carry out an embodiment of the invention.

FIG. 2 illustrates the construction of evaluation system 10 according to an example of an embodiment of the invention, as realized by way of a computer system. Evaluation system 10 performs the operations described in this specification to determine the extreme value of pipeline wall loss (worst case corrosion) of a pipeline. Of course, the particular architecture and construction of a computer system useful in connection with this invention can vary widely. For example, evaluation system 10 may be realized by a computer based on a single physical computer, or alternatively by a computer system implemented in a distributed manner over multiple physical computers. Accordingly, the generalized architecture illustrated in FIG. 2 is provided merely by way of example.

As shown in FIG. 2, evaluation system 10 includes central processing unit 15, coupled to system bus BUS. Also coupled to system bus BUS is input/output interface 11, which refers to those interface resources by way of which peripheral functions P (e.g., keyboard, mouse, display, etc.) interface with the other constituents of evaluation system 10. Central processing unit 15 refers to the data processing capability of evaluation system 10, and as such may be implemented by one or more CPU cores, co-processing circuitry, and the like. The particular construction and capability of central processing unit 15 is selected according to the application needs of evaluation system 10, such needs including, at a minimum, the carrying out of the functions described in this specification, and also including such other functions as may be desired to be executed by computer system. In the architecture of evaluation system 10 according to this example, data memory 12 and program memory 14 are also coupled to system bus BUS, and provide memory resources of the desired type useful for their particular functions. Data memory 12 stores input data and the results of processing executed by central processing unit 15, while program memory 14 stores the computer instructions to be executed by central processing unit 15 in carrying out those functions. Of course, this memory arrangement is only an example, it being understood that data memory 12 and program memory 14 can be combined into a single memory resource, or distributed in whole or in part outside of the particular computer system shown in FIG. 2 as implementing evaluation system 10. Typically, data memory 12 will be realized, at least in part, by high-speed random-access memory in close temporal proximity to central processing unit 15. Program memory 14 may be realized by mass storage or random access memory resources in the conventional manner, or alternatively may be accessible over network interface 16 (i.e., if central processing unit 15 is executing a web-based or other remote application).

Network interface 16 is a conventional interface or adapter by way of which evaluation system 10 accesses network resources on a network. As shown in FIG. 2, the network resources to which evaluation system 10 has access via network interface 16 can include those resources on a local area network, as well as those accessible through a wide-area network such as an intranet, a virtual private network, or over the Internet. In this embodiment of the invention, sources of data processed by evaluation system 10 are available over such networks, via network interface 16. Library 20 stores measurements acquired by in-line inspection (ILI) for selected pipelines in the overall production field or pipeline system; ILI library 20 may reside on a local area network, or alternatively be accessible via the Internet or some other wider area network. It is contemplated that ILI library 20 may also be accessible to other computers associated with the operator of the particular pipeline system. In addition, as shown in FIG. 2, measurement inputs 18 acquired by sampled ultrasonic or radiography (UT/RT) for other pipelines in the production field or pipeline system are stored in a memory resource accessible to evaluation system 10, either locally or via network interface 16.

Of course, the particular memory resource or location in which the UT/RT measurements 18 are stored, or in which ILI library 20 resides, can be implemented in various locations accessible to evaluation system 10. For example, these data may be stored in local memory resources within evaluation system 10, or in network-accessible memory resources as shown in FIG. 2. In addition, these data sources can be distributed among multiple locations, as known in the art. Further in the alternative, the measurements corresponding to UT/RT measurements 18 and to ILI library 20 may be input into evaluation system 10, for example by way of an embedded data file in a message or other communications stream. It is contemplated that those skilled in the art will be readily able to implement the storage and retrieval of UT/RT measurements 18 and ILI library 20 in a suitable manner for each particular application.

According to this embodiment of the invention, as mentioned above, program memory 14 stores computer instructions executable by central processing unit 15 to carry out the functions described in this specification, by way of which UT/RT measurements 18 for a given pipeline are analyzed to determine an estimate of the likely extreme wall loss value for that pipeline. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language, either as a conventional linear computer program or arranged for execution in an object-oriented manner. These instructions may also be embedded within a higher-level application. For example, an embodiment of the invention has been realized as an executable within the ACCESS database application using Visual Basic Algorithm (VBA) instructions to provide output in the form of an EXCEL spreadsheet, which is beneficial because of the relatively low level of user training that is required. It is contemplated that those skilled in the art having reference to this description will be readily able to realize, without undue experimentation, this embodiment of the invention in a suitable manner for the desired installations. Alternatively, these computer-executable software instructions may be resident elsewhere on the local area network or wide area network, accessible to evaluation system 10 via its network interface 16 (for example in the form of a web-based application), or these software instructions may be communicated to evaluation system 10 by way of encoded information on an electromagnetic carrier signal via some other interface or input/output device.

The common approach to estimation of an extreme value is to identify the value of a quantile at the extreme end of a statistical distribution. Of course, for a finite population, the extreme value will literally be the extreme value of the finite set of values. As known in the field of statistics, a quantile is the data value marking the boundaries between consecutive ones of q essentially equal-sized data subsets in the distribution. For the example of a pipeline that is one hundred feet in length, and for which measurements are being considered over one-foot intervals, the extreme value will be derived as the data value at the $99^{th}$ percentile of the distribution. Extreme value generation therefore obviously depends strongly on the choice of the statistical distribution to be used.

A desired result from embodiments of this invention, as practiced, is an estimate of the extreme value of wall thickness loss (worst case corrosion) of a pipeline based on sample measurements taken along that pipeline. Unfortunately, pipeline wall thickness loss measurements along a pipeline do not reliably follow known statistical distributions. Indeed, it has been observed that the distribution of actual pipeline wall thickness loss measurements along a pipeline does not fit any one statistical distribution, but often appears as a mixture of distributions. In addition, this mixture of distributions is not necessarily constant from pipeline to pipeline, which is intuitive given the variation of pipelines in length, material, construction, composition of the fluid carried, frequency and number of supports and couplings and joints, and the like. This erratic statistical behavior is believed to be due to non-uniform susceptibility of the pipeline to corrosion along its length; some portions or locations of pipelines (e.g., near pipeline supports) are more susceptible to corrosion than others. It is therefore unreasonable to expect that a single statistical distribution can accurately represent wall thickness loss along the length of the pipeline.

According to embodiments of the invention, statistics from those pipelines that have been measured along their length, for example by ILI, are used to derive a discriminant function by way of which an optimal distribution can be selected for a pipeline for which only sampled measurements are available. Once the distribution is selected for the sampled pipeline, then an extreme value can be estimated and the confidence intervals for that extreme value estimate can be derived.

According to this embodiment of the invention, the candidate statistical distributions, from which the optimal distribution is selected, are based on ILI measurements taken along the length of the reference pipelines. ILI measurements are especially useful in connection with this invention, because of the ability of ILI technology to obtain thickness measurements at small increments along the length of the pipeline being measured. For purposes of this embodiment of the invention, such ILI measurement can be considered to be virtually, if not literally, "100% inspection" of the wall thickness or wall thickness loss along the measured length of the pipeline. This high degree of coverage provides an accurate measure of the minimum wall thickness along that pipeline, which in turn enables the corresponding statistical distribution of ILI measurements to provide a reasonable extreme value estimate for a pipeline for which only sampled measurements are available, according to this embodiment of the invention. It is contemplated that these candidate statistical distributions may be based on measurements acquired by technologies other than ILI, or by ILI measurements at less than virtually 100% coverage, so long as the measurement coverage of those reference pipelines substantially characterizes the relevant length of the pipeline to an extent that one can be highly confident (e.g., on the order of 99% confident) that the true largest possible wall thickness loss has been observed. Full measurement coverage obtained by in-line inspection of the reference pipelines is, of course, particularly useful in connection with this embodiment of the invention, as that approach will provide the highest degree of confidence in the extreme value measurement for the reference pipelines.

Figure 3:
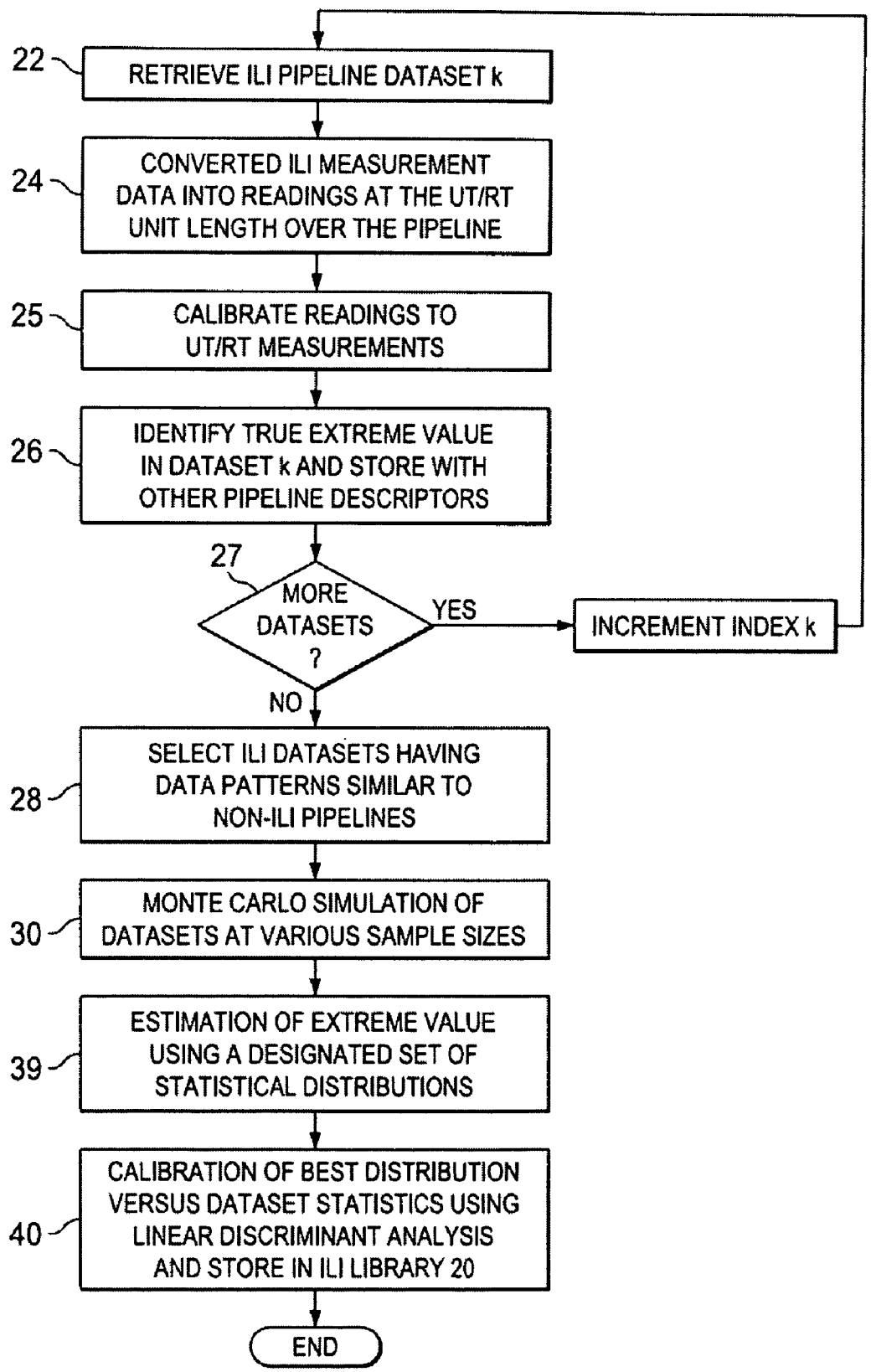
FIG. 3 is a flow diagram illustrating the derivation of a discriminant function from an in-line inspection calibrated measurement library, according to an embodiment of the invention.

According to the embodiment of the invention illustrated in FIG. 2, ILI library 20 includes measurement data for each of those pipelines upon which in-line inspection (ILI) has been carried out, and also includes statistical information based on those measurements as well as other parameters regarding those pipelines themselves. The pipelines for which ILI measurements may be useful include those pipelines within the same system as the pipeline of interest for which an extreme value estimate is being made, and also pipelines in other systems that can be considered as possibly analogous. The properties of Monte Carlo samples, at various sample sizes, taken from these datasets of ILI measurements stored in ILI library 20, along with the other pipeline descriptors, will be used to derive a discriminant function for selecting a statistical distribution from sample statistics and other parameters for other pipelines, according to this embodiment of the invention. Referring now to FIG. 3, the derivation of such a discriminant function from ILI library 20 of ILI measurements acquired on one or more pipelines in the overall system, according to this embodiment of the invention, will now be described.

According to this embodiment of the invention, evaluation system 10 may itself build ILI library 20 and derive the discriminant function, or alternatively another computer system may build ILI library 20 and derive the discriminant function, with the discriminant function then communicated or otherwise made accessible to evaluation system 10. As such, the particular computer system that carries out the processing illustrated in FIG. 3 to derive the discriminant function is not of particular importance in connection with this invention. As evident from the nature of the processing of FIG. 3, derivation of the discriminant function need only be done once, in advance of the operations to be carried out by evaluation system 10 in analyzing sampled measurements according to this embodiment of the invention. Additional ILI measurement datasets that are acquired can be processed and added into ILI library 20. In this event, the discriminant function can then be recalculated, to be further updated with the additional distributions and statistics from the new datasets.

In process 22, the in-line inspection data for a pipeline are retrieved. The in-line inspection dataset k retrieved in process 22 includes measurements taken along the entire length of a pipeline, at a spacing determined by the particular ILI technology and system used to acquire the data. These data may be retrieved in process 22 from a memory resource or over a network, or otherwise received by the operative computer system involved in deriving the discriminant function.

For purposes of this embodiment of the invention, it is useful if the ILI measurements retrieved in process 22 are expressed in incremental lengths consistent with UT/RT sample measurements taken of other pipelines. According to this embodiment of the invention, therefore, in process 24, the ILI measurement data are converted into measurements at a unit length corresponding to the unit length of sampled measurements. For example, the length of interest for a sampled UT/RT measurement may be a one-foot interval along the length of a pipeline. It is likely that ILI measurements do not correspond to one-foot intervals, but instead present data more finely (i.e., effectively continuous) than the sampled UT/RT measurements. Accordingly, in process 24, the operative computer system converts the ILI measurement data into the desired unit of measurement (e.g., percent wall loss) at the unit length of interest (e.g., one-foot lengths) corresponding to the UT/RT measurements carried out by the measurement operator. This conversion can be carried out by conventional techniques, for example by selecting and storing the maximum wall loss measurement within each of the desired intervals.

It has been observed, in connection with this invention, that pipeline wall loss measurements vary among measurement technology. More specifically, it has been observed that a bias exists between ILI measurements and those obtained from UT/RT inspections (with UT and RT measurements observed to correspond well with one another). This bias is somewhat difficult to characterize because ILI measurement of wall loss for a given pipeline typically indicates a far greater percentage of length of minimal thickness loss than do sampled measurements by way of UT or RT for that same pipeline. This high percentage of minimal loss renders the derivation of a rigorous calibration equation somewhat difficult. However, because the goal of pipeline integrity monitoring, by either technology, is primarily concerned with detecting the extreme value of wall loss (i.e., the location of first failure), a useful calibration function can be derived by comparing only those measurements of relatively high (e.g., >20%) wall loss among the various technologies. This truncation of the measurements can provide a useful calibration function. Accurate calibration renders the ILI measurements useful in characterizing the distribution of the UT/RT measurements according to this embodiment of the invention, as will be described below.

In one example, a calibration of ILI wall loss measurements to UT wall loss measurements has been performed from a regression of maximum wall loss values for several pipelines, as detected by ILI measurements, with maximum wall loss values for those same pipelines as detected by UT sampling. This regression used only those ILI values greater than 20% wall loss, and excluded obvious exceptions. In addition, this regression does not require the ILI measurement to be at the same physical location along the pipeline as a corresponding UT (or RT) measurement. The result of this regression provided the following relationship of maximum wall loss thickness $UT_{max}$ as measured by sampled ultrasonic tomography to the corresponding ILI maximum wall loss thickness as measured $ILI_{max}$:

$$UT_{max} = 2.18 + 1.18(ILI_{max})$$

Of course, it is contemplated that a different calibration scheme may be applied, depending on the particular measurement technologies and apparatus used in each case, differences in the pipelines and the nature of the fluid carried, whether a higher order calibration is desired, and the like.

Once a calibration function is defined, for example from analysis of a reasonable number of pipelines with both ILI and UT or RT wall loss measurements, calibration process 25 is performed over the ILI wall loss measurements for pipeline dataset k according to that function.

The true extreme value of wall thickness loss measurement indicated by the converted and calibrated ILI measurements will be used in deriving the discriminant function, according to this embodiment of the invention. Accordingly, that extreme value is identified for dataset k, and stored in memory in a manner associated with dataset k, in process 26. In addition, according to this embodiment of the invention, certain parameters about the physical pipeline can be useful in deriving the discriminant function. Examples of these pipeline descriptors include the length of the pipeline, the diameter of the pipeline, whether a water phase is present in the fluid carried by the pipeline, whether an oil phase is present, and the like. These parameters are also stored in memory in association with dataset k, in process 26.

Decision 27 determines whether additional ILI datasets remain to be converted and calibrated. If so (decision 27 is YES), dataset index k is incremented in process 29, and the next dataset k is retrieved (process 22), converted into the desired increments of pipeline length (process 24), calibrated to UT/RT measurements (process 25), and its extreme value of wall thickness loss identified and stored along with pipeline descriptors (process 26). Upon completion of these processes for all ILI datasets to be considered (decision 27 is NO), control passes to process 28 for determination of which of the ILI datasets are suitable for use in deriving extreme value estimators.

In process 28, the operative computer system determines which of the converted and calibrated datasets are suitable for use in extreme value estimation, by selecting those datasets that exhibit patterns, in their measurement values, that are similar to the sampled measurement values obtained by UT/RT from other pipelines that are to be investigated. According to this embodiment of the invention, as will be described below, the discriminant function used to select an optimal statistical distribution is not based on the fit of the statistical distribution over the entire distribution of measurements, but rather will be based on the accuracy of the statistical distribution in estimating the extreme value of worst case corrosion. As noted above, the actual distribution of wall thickness loss measurements typically appears to be a mixture of distributions. Given these factors, an ILI dataset that is heavily weighted with zero-wall loss measurements will not be particularly helpful in selecting a statistical distribution from which the extreme value is to be estimated. Accordingly, process 28 eliminates those datasets for which the converted and calibrated ILI measurements do not meet a similarity criterion. An example of a similarity criterion useful in process 28 is a percentage threshold of non-zero wall loss measurements. For example, if more than 50% of the converted calibrated wall thickness loss measurements of a dataset are zero-valued, that dataset will be eliminated from the derivation of the discriminant function by process 28.

Once the suitable ILI datasets for extreme value estimation are identified in process 28, Monte Carlo simulated sampling of these datasets at various sample sizes is then performed, in process 30. The operation of process 30 according to this embodiment of the invention will now be described in connection with the flow diagram of FIG. 4.

Figure 4:
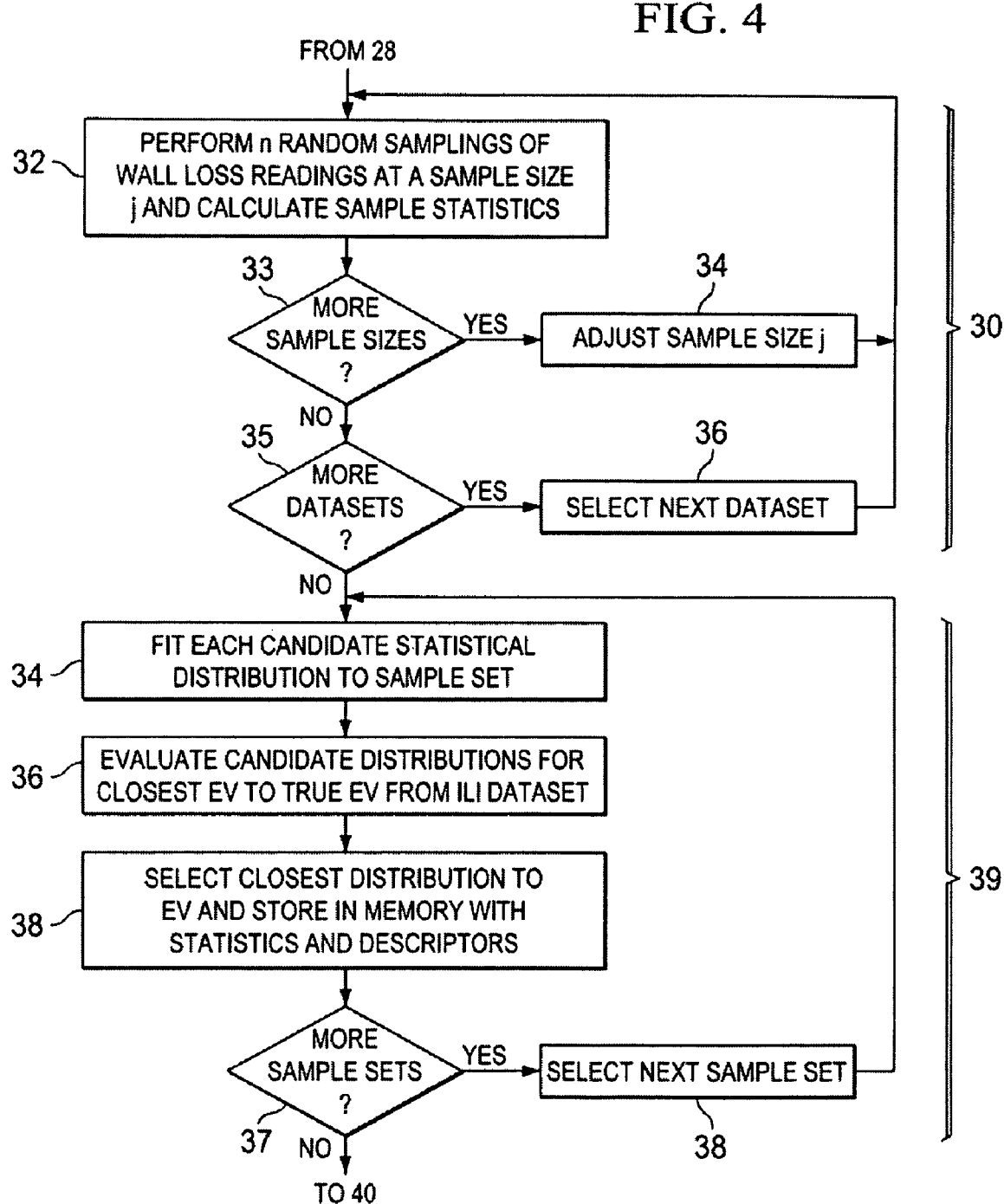
FIG. 4 is a flow diagram illustrating the evaluation of sample sets with candidate statistical distributions in the process of FIG. 3, according to an embodiment of the invention.

Process 30 begins, as shown in FIG. 4 with the random sampling of calibrated ILI wall loss measurements in pipeline dataset k, in process 32. These random samples correspond to wall thickness measurements (expressed, in this embodiment, as percentage of wall thickness loss) at random locations along the length of the pipeline. Each instance of process 32 samples the distribution of calibrated ILI measurements in pipeline dataset k to a specified sample size j; for best results, the sample size j will correspond generally to a range of possible sample sizes of UT/RT measurements for pipelines in the field. For example, in practice, the method of this embodiment of the invention is most useful in connection with UT/RT measurement sample sizes ranging from about ten to about one thousand. In addition, process 32 may reduce the number of random samplings performed at higher sample sizes j, as these higher sample sizes will exhibit less variability among one another (and will thus give the same result). Also in process 32, certain sample statistics that may prove useful in deriving the discriminant function are also calculated for this sample set, and stored in memory. These statistics include at least those statistics that will be useful in fitting various statistical distributions to the sample values (e.g., mean, median, standard deviation or variance), as well as other statistics that may assist the discriminant calculation (e.g., 75% quantile value, kurtosis, skewness, sample size, maximum sample value, etc.). This Monte Carlo simulated sampling of the calibrated ILI measurements, at this same sample size, and calculation of the relevant statistics, are repeated n times in process 32, with n being a relatively modest number (e.g., on the order of ten), and the results recorded for each sampling. Decision 33 is performed to determine whether additional sample sizes are to be analyzed for dataset k; if so (decision 33 is YES), sample size j is adjusted in process 34, and process 32 is repeated for this new sample size. Upon obtaining the desired number of samples at all of the desired sample sizes for a dataset k, decision 35 determines whether additional datasets remain to be sampled. If so (decision 35 is YES), dataset index k is incremented (process 36), and sampling process 32 is performed on the next dataset.

Once all the desired sample sets are obtained via process 32 at all desired sample sizes for all of the datasets to be considered (decision 35 is NO), these sample sets are then used to determine the one statistical distribution, out of a set of candidate statistical distributions, that best predicts the extreme value of worst case corrosion for each sample set. This determination is made by estimating the extreme value using each of these statistical distributions as applied to the sample sets, which is performed in process 39 (FIG. 3) according to this embodiment of the invention. It has been observed, in connection with this invention, that the parameter of wall thickness loss along the length of the pipeline does not necessarily follow a single statistical distribution. Rather, it has been observed that, in many cases, the distribution of wall loss measurements along a pipeline appears to be a mixture of distributions. Considering these observations, the selection of a statistical distribution is based on the "goodness of fit" of estimates of the extreme value from the statistical distributions to the actual extreme value of the pipeline, rather than the goodness of fit of the statistical distribution to the entire set of sample values.

It is contemplated that the set of candidate statistical distributions to be evaluated for extreme value estimation, in this embodiment of the invention, will be preselected. It has been observed, in connection with this invention, that statistical distributions that are characterizable by two parameters are best suited for worst case corrosion estimation, as opposed to three-parameter statistical distributions such as the Generalized Pareto Distribution and the Generalized Extreme Value (GEV) Distribution. FIGS. 5a through 5d illustrate the shapes of some statistical distributions that are contemplated to be generally useful in connection with this embodiment of the invention. These statistical distributions include the Minimum Extreme Value Distribution, the Logisitic Distribution, the Maximum Extreme Value Distribution, and the Weibull Distribution, shown in FIGS. 5a through 5d, respectively. For the description of this embodiment of the invention, these four statistical distributions will be the candidate statistical distributions.

Given the set of candidate statistical distributions, each of the candidate statistical distributions are evaluated for each of the sample sets. Referring again to FIG. 4, this operation begins, for a given sample set (each sample set being considered individually, without regard to the ILI dataset to which it belongs except by way of reference to its true extreme value and any associated pipeline descriptors that were stored in process 26), in process 34. In this process 34, each candidate statistical distribution is fit to the sample set by way of the statistics calculated for that sample set in process 32. This fitting of the candidate statistical distributions to the sample sets is contemplated to be performed by conventional statistical or mathematical computer software, typically applying maximum-likelihood techniques, and executed by evaluation system 10 or such other computer system that is operating to derive the discriminant function; various conventional computer software programs for carrying out this function are well-known to those skilled in the art. This fitting is performed for each of the candidate statistical distributions for the current sample set, in process 34.

In process 36, each of the candidate statistical distributions are interrogated to obtain an estimate of the extreme maximum value of wall thickness loss. As mentioned previously, the evaluation of a distribution to obtain an extreme value amounts to an evaluation of the distribution at a specific quantile. In this embodiment of the invention, this extreme value quantile has a relationship to the overall length of the pipeline. For example, if a pipeline has a length of 20,000 feet, and if measurements (as converted) are being considered at one-foot intervals, then the extreme value will be that value, in the statistical distribution at the quantile:

Extreme value quantile=100*(1−1/20,000)=99.995%

In general, the extreme value quantile is thus determined as:

Extreme value quantile=100*(1−1/length)

The evaluation of each candidate statistical distribution, in process 36, can be performed using conventional statistical computer software as known in the art. An example of such computer software that is particularly useful in this evaluation process 36 is the SPLIDA statistical software package developed by Dr. William Meeker of Iowa State University; the SPLIDA software package is implemented in the S-Plus statistical programming language, and follows the methodologies, described in Meeker and Escobar, *Statistical Methods for Reliability Data* (Wiley-Interscience, New York, 1998). FIG. 5c illustrates an example of a result from the SPLIDA statistical software package in identifying the value at the extreme value quantile. In this example, the software package returns an extreme value estimate of 45% wall thickness loss, taken at the 99.995% quantile. The confidence level distribution for this estimate is illustrated in FIG. 5e, and shows that this extreme value ranges from 38% to 53% wall thickness loss, at a 95% confidence level.

Figure 5G:
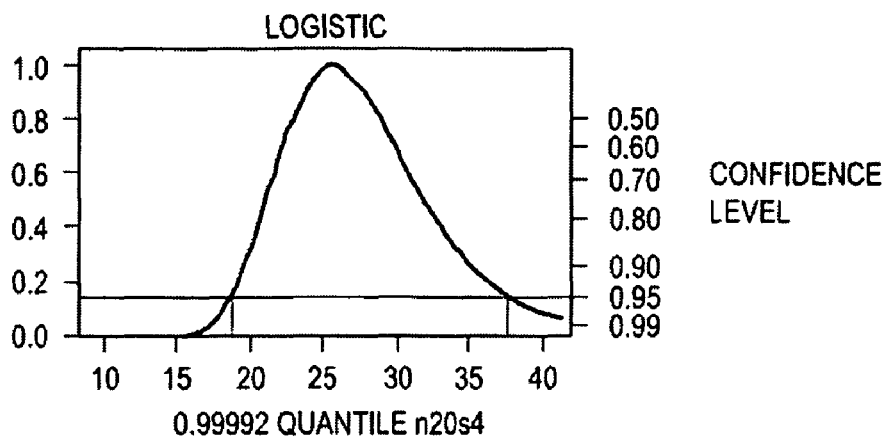
Figure 5H:
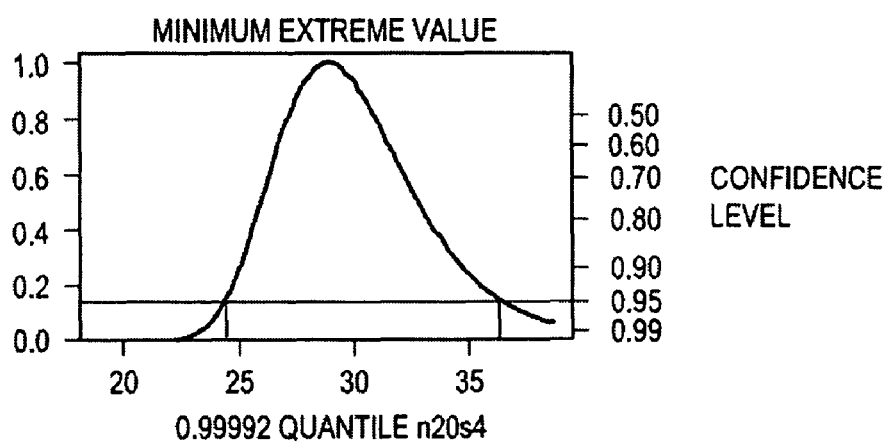
Figure 5I:
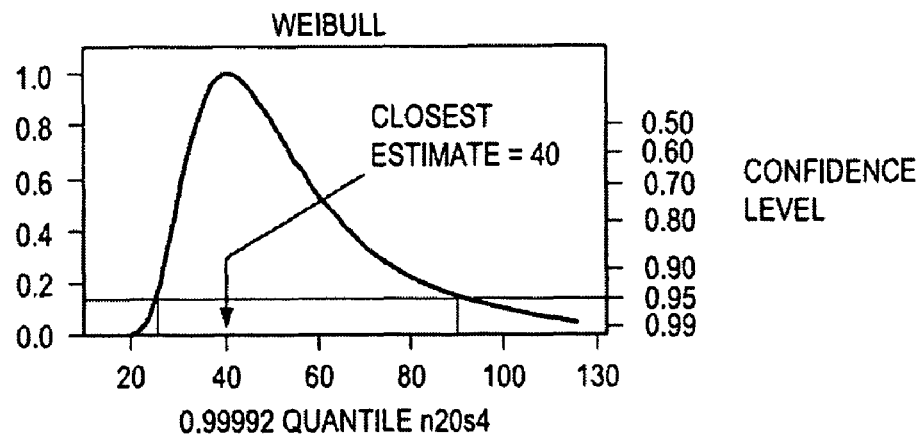

In process 38, the extreme value quantile calculated for each candidate statistical distribution is compared to the true extreme value that was stored for this dataset k in process 26. This comparison of process 38 may be a simple arithmetic comparison of the most likely extreme value determined in process 36 with the true extreme value; alternatively, the confidence level about the calculated extreme value may be considered. FIGS. 5f through 5i illustrate examples of comparison process 38, for an example in which the true extreme value of wall thickness loss was 38% as measured by ILI (and calibrated to UT/RT). FIG. 5f illustrates that the extreme value indicated by the Maximum Extreme Value distribution was 30%. FIG. 5g illustrates that the extreme value indicated by the Logistic distribution was 26%. FIG. 5h illustrates that the extreme value indicated by the Minimum Extreme Value distribution was 29%. FIG. 5i illustrates that the extreme value indicated by the Weibull distribution was 40%, which of course is the closest of these four candidate distributions in this example. An identifier of the closest estimating candidate distribution is then stored in memory, along with the calculated sample statistics and pipeline descriptors associated with the ILI dataset k from which this sample set was taken, also in process 38. An example of the result of process 38, for ten sample sets that, for example, are all derived from the sample pipeline dataset, is:

| Mean | Median | Q3  | Max  | N  | Stdev | Skewness | Kurtosis | LengtH | Diameter | Serv_PW | Serv_PO | Serv_O | Best Dist |
|------|--------|-----|------|----|-------|----------|----------|--------|----------|---------|---------|--------|-----------|
| 4.6  | 4.2    | 5.7 | 18.2 | 10 | 5.3   | 2.0      | 5.1      | 12754  | 24       | 0       | 0       | 1      | E         |
| 5.1  | 4.1    | 5.7 | 15.7 | 10 | 4.0   | 2.4      | 6.4      | 12754  | 24       | 0       | 0       | 1      | E         |
| 4.6  | 4.7    | 5.1 | 13.0 | 10 | 3.4   | 1.7      | 4.3      | 12754  | 24       | 0       | 0       | 1      | E         |
| 4.1  | 3.7    | 5.4 | 11.2 | 10 | 3.1   | 1.2      | 2.4      | 12754  | 24       | 0       | 0       | 1      | W         |
| 3.1  | 4.0    | 5.0 | 5.8  | 10 | 2.4   | −0.3     | −2.1     | 12754  | 24       | 0       | 0       | 1      | W         |
| 8.5  | 3.9    | 7.4 | 29.4 | 20 | 10.3  | 1.4      | 0.4      | 12754  | 24       | 0       | 0       | 1      | S         |
| 6.5  | 3.8    | 5.2 | 26.5 | 20 | 8.0   | 2.0      | 2.6      | 12754  | 24       | 0       | 0       | 1      | L         |
| 6.8  | 3.9    | 5.0 | 28.9 | 20 | 7.8   | 1.9      | 2.6      | 12754  | 24       | 0       | 0       | 1      | L         |
| 5.3  | 2.3    | 4.1 | 32.1 | 20 | 8.0   | 2.6      | 6.8      | 12754  | 24       | 0       | 0       | 1      | E         |
| 4.4  | 3.5    | 4.7 | 23.6 | 20 | 5.4   | 2.8      | 9.0      | 12754  | 24       | 0       | 0       | 1      | E         |

In this example, the number "N" is the sample size of the particular sample set. The pipeline descriptors of "Serv PW", "Serv PO", and "Serv O" indicate, respectively, whether the pipeline service includes produced water, produced oil (i.e., oil in the pipeline as pumped from the ground), and "oil" (i.e., oil in the pipeline from the outflow of a separator). Other statistics and pipeline descriptors in this table are self-explanatory. The best extreme value fit statistical distribution is illustrated, for each sample set, as the category response in the last column: "E" indicates the Maximum Extreme Value distribution, "W" indicates the Weibull distribution, "S" indicates the Minimum Extreme Value distribution, and "L" indicates the Logistic distribution.

If additional sample sets remain to be analyzed (decision 37 is YES), the next sample set is selected (process 39) and evaluation processes 34, 36, 38 are repeated for the next sample set. Upon all sample sets being evaluated and the best candidate statistical distribution identified (decision 37 is NO), process 39 is complete, and the discriminant function can now be derived in process 40 (FIG. 3).

According to this embodiment of the invention, the discriminant function will be derived in the form of a set of linear equations. A useful step, in this regard, is to initially identify any of the sample statistics stored for each dataset that tend to correlate with one another, so that but one of those correlating statistics are preferably removed from the discriminant function derivation. Otherwise, those correlating statistics would tend to be overemphasized in the resulting function. For example, in one example of this method, kurtosis correlated with skewness and was therefore dropped from the analysis.

Figure 5J:
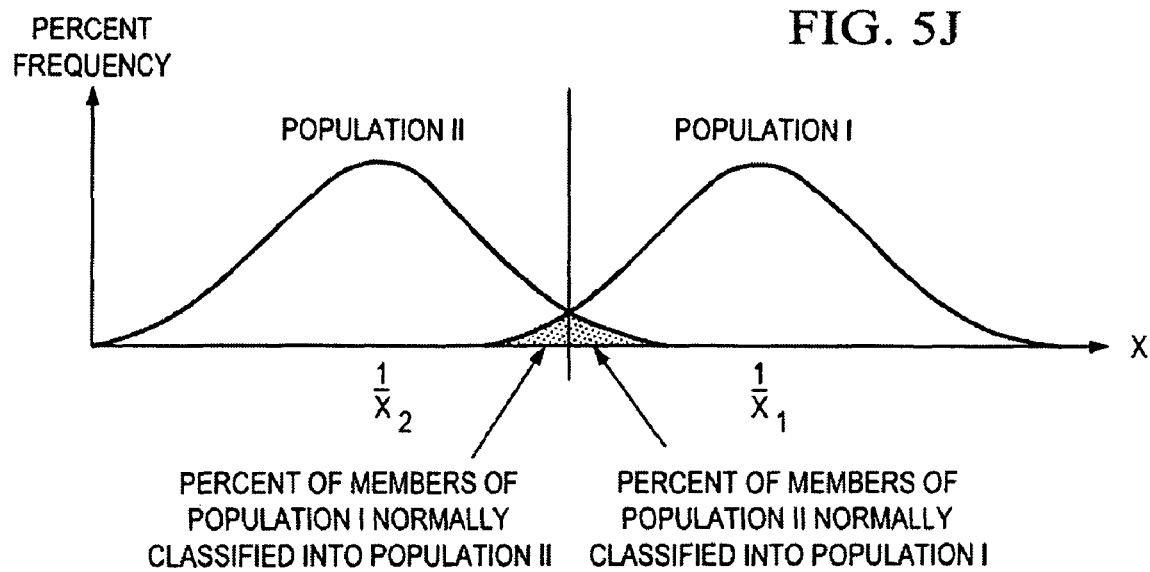
FIG. 5j illustrates an example of a conventional discriminant function.

The statistical methodology for deriving a discriminant function in this situation having a categorical response (the best fit statistical distribution) is called linear discriminant analysis, approaches to which are described in Afifi et al., *Computer-Aided Multivariate Analysis* 4$^{th}$ *Edition* (Chapman&Hall/CRC, Boca Raton, 2004). FIG. 5*j* illustrates simplified illustration of this type of problem by way of a figure from the Afifi reference, for the example of a two-response set (Population I and Population II) with a single predictor variable x. It is the value of predictor x that determines whether a particular member ought to be assigned to Population I or Population II. The discriminant function in this example is simply the vertical line shown in FIG. 5*h* between the two populations.

According to this embodiment of the invention, the discriminant function will be more complex than the simple example shown in FIG. 5*j*, both in the number of populations to be separated, and also in the number of predictor variables. However, modern computing capability is fully capable of deriving the appropriate discriminator function, as a set of linear equations, using conventional techniques. It has been observed, in connection with this invention, that some of the prediction behavior is non-linear, and as such it is useful to evaluate both the linear and the quadratic behavior of all of the possible predictors. To improve efficiency, according to this embodiment of the invention, logarithms may be used to express some of the predictors, simplifying the equations. An example of a resulting discriminant equation derived according to an example of this embodiment of the invention, for an example of 538 datasets considered from eighteen ILI pipelines, is shown in Table 1:

TABLE 1

| | Discriminant Function Analysis Summary No. of vars in model: 10: Grouping: Distribution (4 grps) | | |
|---|---|---|---|
| N = 536 | F-remove (3,525) | p-level | 1-Toler. (R-Sqr.) |
| Max | 4.3 | 0.0055 | 0.90 |
| Stdev | 29.6 | 0.0000 | 0.87 |
| Skewness | 28.2 | 0.0000 | 0.81 |
| Diameter | 7.3 | 0.0001 | 0.30 |
| log_mean | 3.3 | 0.0192 | 0.90 |
| ln_q3+ | 13.0 | 0.0000 | 0.82 |
| log_n | 4.6 | 0.0036 | 0.64 |
| skew_sq | 8.7 | 0.0000 | 0.40 |
| stdev_sq | 10.2 | 0.0000 | 0.68 |
| log_mean_q | 9.4 | 0.0000 | 0.55 |

As known in the art, smaller p-level values in this table correspond to higher levels of significance as a discrimination variable. Those parameters (statistics and pipeline descriptors) that are not useful in determining the classification of the statistical distributions are not shown in this table. For example, in this example, the pipeline descriptors of pipeline length and also of pipeline service indicators (produced water, produced oil, and oil) did not affect the accuracy of the statistical distribution prediction. It is contemplated, however, that such descriptors may be important in some pipelines, and as such are suitable for consideration as important predictors in other situations.

Given the discriminant analysis that is shown in Table 1, conventional mathematical operations can be executed by evaluation system 10 or such other computer system that is being used to derive the discriminant function and store that discriminant function in ILI library 20, in process 40. According to this embodiment of the invention, process 40 creates and stores a set of classification equations, one for each candidate statistical distribution. An example of these classification equations is shown in Table 2:

TABLE 2

| | Classification Functions; grouping: Distribution | | | |
|---|---|---|---|---|
| Variable | S p = .232 | L p = .242 | E p = .284 | W p = .242 |
| Max | −2.425 | −2.318 | −2.287 | −2.349 |
| Stdev | 1.299 | 0.667 | −0.091 | −0.314 |
| Skewness | 26.49 | 26.74 | 27.79 | 30.04 |
| Diameter | 1.104 | 1.137 | 1.132 | 1.249 |
| log_mean | 142.6 | 144.2 | 152.3 | 150.7 |
| ln_q3+ | 19.41 | 17.86 | 14.92 | 18.39 |
| log_n | 23.73 | 22.39 | 21.97 | 22.43 |
| skew_sq | 3.747 | 3.479 | 3.667 | 4.175 |
| stdev_sq | 0.0628 | 0.0551 | 0.1256 | 0.1082 |
| log_mean_q | 51.23 | 43.34 | 44.00 | 58.26 |
| Constant | −113.5 | −106.5 | −103.2 | −114.4 |

The discriminant function according to this embodiment of the invention is a set of linear equations, each linear equation associated with one of the candidate statistical distributions. In the example of Table 2, the linear equation for each candidate distribution is the simple linear combination of each of the numbers in a column of Table 2 with the data values for the pipeline of the interest corresponding to the sample statistics or pipeline descriptor for each row. An additive constant is also included in each linear equation ("Constant") at the bottom of the table. For example, the linear equation for the Minimum Extreme Value distribution ("S") would be expressed as:

"$S$"$=-2.425(\text{Max})+1.200(\text{Stdev})+26.49(\text{Skewness})+$
$1.104(\text{Pipeline\_diameter})+142.6(\log_{10}(\text{Mean}))+$
$19.41(\ln(Q3+))+23.73(\log_{10}(n))+3.747(\text{skew}^2)+$
$51.23((\log_{10}(\text{Mean}))^2)-113.5$ This discriminant function of the set of linear equations (which may include squared or logarithmic terms based on statistics or pipeline descriptors) will be applied to the sample statistics and pipeline descriptor values for a sampled pipeline, by evaluating each of the equations. The statistical distribution which returns the highest value from its linear equation as applied to the sample statistics and pipeline descriptors will be the selected statistical distribution for determining the worst case corrosion for that sampled pipeline. Upon completion of process 40, sampled values of wall thickness loss for other pipelines can now be analyzed for their worst case corrosion value, as will now be described relative to FIG. 6.

Figure 6:
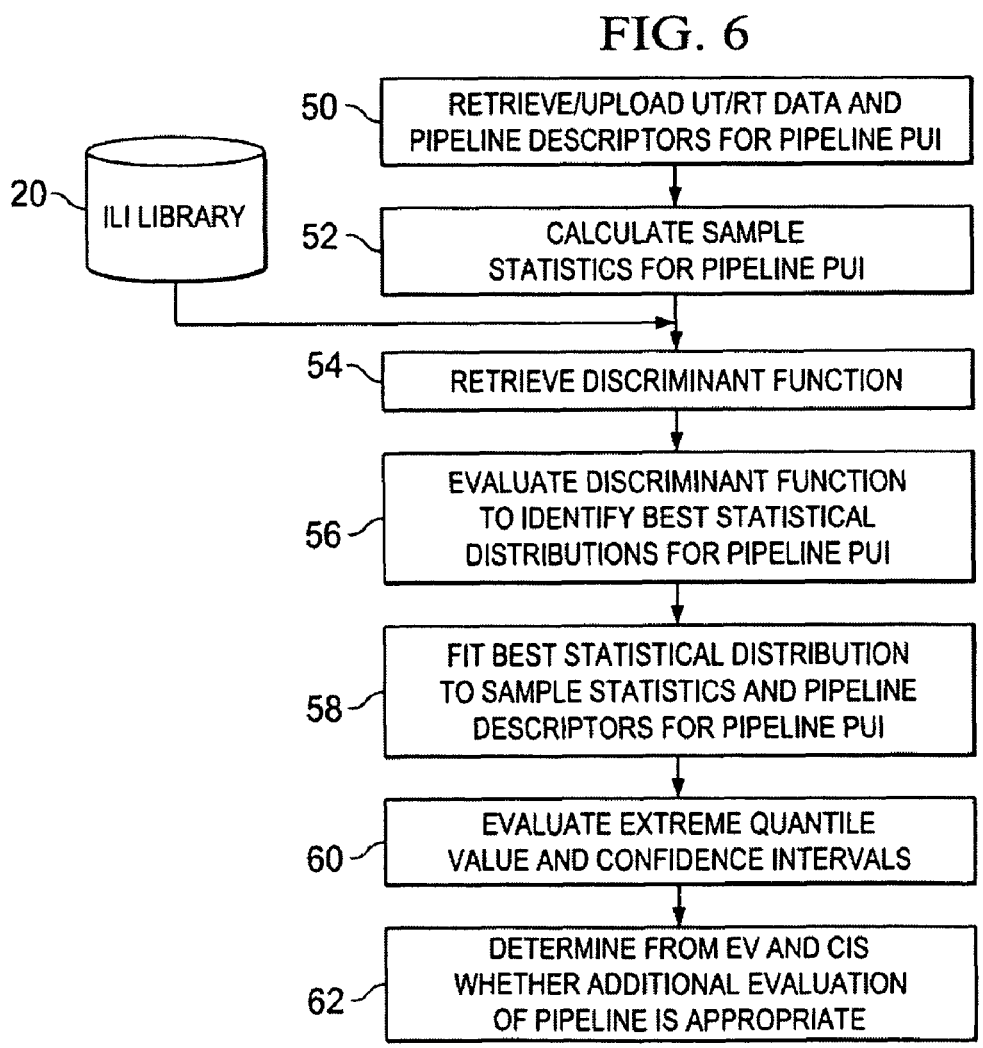
FIG. 6 is a flow diagram illustrating the estimation of worst case corrosion for a pipeline for which sampled measurements of wall thickness loss have been acquired, according to an embodiment of the invention.

According to this embodiment of the invention, once the discriminant function based on ILI datasets has been derived and stored in ILI library 20, sample measurements of pipelines other than those for which ILI has been performed can now be analyzed to obtain an estimate of the worst case corrosion in those sampled pipelines. FIG. 6 illustrates the overall operation of a method of analyzing UT/RT measurements to obtain an estimate of such an extreme value, according to this embodiment of the invention. It is contemplated that this process will be carried out by evaluation system 10, an example of which is described above relative to FIG. 3, which may be a workstation operated by a human analyst determining the sufficiency of the UT/RT sample coverage for one or more pipelines. As mentioned above in connection with that description of evaluation system 10, it is also contemplated that the computational resources and components carrying out this process may be deployed in various ways, including by way of a web application or other distributed approach.

According to this embodiment of the invention, the analysis of UT/RT measurements for a particular pipeline under investigation (this pipeline referred to herein as "pipeline PUI") begins with the retrieval of the sampled UT/RT measurements from data source 18, shown as process 50 of FIG. 6. Pipeline PUI is typically an "unpiggable" pipeline, for which only sampled measurements of wall loss have been obtained. In this embodiment of the invention, the retrieved data for pipeline PUI include an individual wall loss value for each of a number of samples acquired at locations along pipeline PUI, for example by way of ultrasonic tomography (UT) or radiography (RT), or some other measurement technology. These sample UT/RT measurements may be pre-processed so as to be expressed as a figure of wall thickness loss (e.g., percentage wall loss). In this described example, each UT/RT sample is considered as the maximum percentage wall loss detected over a relatively small interval (e.g., one foot) of the length of pipeline PUI, although other measurements may also be taken or used. The sample interval of the UT/RT measurements should match the interval to which the ILI measurement data were transformed (process 40 of FIG. 4). The data retrieved in process 50 should also include the length of pipeline PUI, the number of UT/RT samples acquired, the diameter of pipeline PUI, and other pipeline descriptors as will be applied to the discriminant function described above.

Upon retrieval of the UT/RT measurement data for pipeline PUI, evaluation system 10 next calculates sample statistics based on the UT/RT sample measurements retrieved, in process 52. These sample statistics include those statistics that are factors in the discriminant function derived from the ILI datasets, as described above. It is contemplated that these sample statistics calculated in process 52 will generally include common statistics such as mean, median, standard deviation, skewness, and the like.

In process 54, evaluation system 10 accesses ILI library 20 to retrieve the discriminant function, in the form of a set of linear equations according to this embodiment of the invention. As described above, these linear equations that make up the discriminant function enable the selection of the most appropriate candidate statistical distribution for evaluating the extreme value of worst case corrosion for pipeline PUI. Process 56 is next executed by evaluation system 10 to apply the sample statistics and pipeline descriptors for pipeline PUI to the discriminant function retrieved in process 54. In this embodiment of the invention, in which the discriminant function is derived as a set of linear equations, one equation for each of the candidate statistical distributions, process 56 involves the evaluation of each of the linear equations with the sample statistics and pipeline identifiers for pipeline PUI, and a comparison of the evaluated result from each of those linear equations to identify the equation returning the largest-valued result. The candidate statistical distribution associated with the largest-valued result of the discrimination function evaluation is, according to this embodiment of the invention, the best one of the candidate statistical distributions for accurately predicting the extreme value of worst case corrosion for pipeline PUI.

In process 60, once the statistical distribution is selected in process 58, evaluation system 10 evaluates an estimate of the extreme quantile value for pipeline PUI, to provide an estimate of the worst case corrosion. Evaluation process 60, as described above for the ILI datasets, involves first fitting the selected statistical distribution to the sample UT/RT values for pipeline PUI, for example by evaluation system 10 executing conventional statistical computer software applying maximum-likelihood functions, as known to those skilled in the art. Once the distribution is fit to the sample data, this distribution is used to obtain an estimate of the extreme maximum value of wall thickness loss (worst case corrosion). As discussed above, in this embodiment of the invention, the extreme value evaluation amounts to an evaluation of the distribution at a specific quantile that is related to the overall length of pipeline PUI:

$$\text{Extreme value quantile} = 100*(1-1/\text{length})$$

The SPLIDA statistical software package referred to above is well-suited for evaluating the extreme value quantile in process 60 according to this embodiment of the invention; of course, those skilled in the art will readily recognize that other software packages and computer programs are also available or can be readily developed to evaluate this extreme value quantile from the selected statistical distribution. Also according to this embodiment of the invention, evaluation system 10 also returns one or more confidence levels and their associated intervals about the calculated extreme value. The results returned from process 60 are similar to those discussed above relative to FIG. 5e, in that the peak of the distribution of extreme values corresponds to the worst case corrosion, with an interval surrounding that peak identified at one or more confidence levels.

The extreme value of worst case corrosion, and the confidence level and associated interval, are evaluated by a system user or by programmed operation of evaluation system 10 itself, in process 62, to determine whether the degree of precision with which the worst case corrosion is identified in process 60 is adequate for the analyst's purposes. If so, the process is complete and another pipeline under investigation can be similarly analyzed. If the worst case corrosion value is sufficiently high, in the opinion of an expert user or relative to a pre-programmed limit at evaluation system 10, other action such as performing additional statistical assessment of the sampled data already obtained for pipeline PUI, and perhaps acquiring new or additional sample data, can be performed to define the appropriate action to be taken in light of the worst case corrosion in pipeline PUI. The appropriate actions to be taken may also depend on the precision of the estimate at the desired confidence level, if the value of the worst case corrosion determined in process 60 is somewhat high.

Important benefits in the monitoring of pipeline integrity in a large scale pipeline system can be obtained according to this invention. The operator can obtain a realistic estimate of worst case corrosion from sampled pipeline wall thickness loss measurements through the use of this invention, without relying on unsupportable assumptions about the statistical distribution of wall loss along the pipeline, and without relying on fluid and material models with unrealistic or unsupportable underlying assumptions. By providing a relatively quick and efficient evaluation of the worst case corrosion, along with a confidence interval at one or more confidence levels, the operator of the production field or pipeline system can more efficiently perform the necessary monitoring and in-depth statistical analysis to ensure a suitable level of integrity, by focusing measurement and analytical resources where most needed.

While the present invention has been described according to its embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A method of estimating the integrity of a pipeline, comprising the steps of:
   receiving sampled measurement data of pipeline wall thickness loss for the pipeline, the measurement data obtained at a plurality of sample locations along the pipeline;
   calculating sample statistics of the sampled measurement data;
   applying the calculated sample statistics to a discriminant function, the discriminant function arranged to identify one of a plurality of candidate statistical distributions for accuracy in estimating an extreme value of pipeline wall thickness loss, each of the plurality of candidate statistical distributions based on wall thickness loss measurements of a corresponding one of a plurality of reference pipelines;
   operating a computer system to evaluate an extreme value quantile of the identified candidate statistical distribution as fit to the sampled measurement data to obtain an estimate of an extreme value of pipeline wall thickness loss for the pipeline.

2. The method of claim 1, further comprising:
   obtaining pipeline descriptors for the pipeline;
   and wherein the applying step also applies the pipeline descriptors to the discriminant function.

3. The method of claim 1, wherein the discriminant function comprises a plurality of linear equations, each associated with a candidate statistical distribution.

4. The method of claim 1, further comprising:
   deriving the discriminant function from Monte Carlo sampling of inline inspection measurement datasets for the plurality of reference pipelines.

5. The method of claim 4, wherein the deriving step comprises:
   identifying an extreme value of pipeline wall thickness loss in each of the plurality of datasets;
   for each of the plurality of datasets, at each of a plurality of sample sizes, randomly sampling each of the datasets one or more times, to derive a plurality of reference sample sets;
   for each of the reference sample sets:
      calculating one or more sample statistics for the sample set;
      evaluating an extreme value quantile using each of the plurality of candidate statistical distributions as fit to the sample set, to obtain an estimate of an extreme value of pipeline wall thickness loss;
      comparing the evaluated extreme value quantile from each of the plurality of candidate statistical distributions to the extreme value of pipeline wall thickness loss for the dataset from which the reference sample set is taken; and
   then, for each of the datasets, identifying one of the candidate statistical distributions for which the evaluated extreme value quantile is closest to the extreme value of pipeline wall thickness loss for the dataset from which the reference sample set is taken; and
   for each of the candidate statistical distributions, operating a computer system to derive a discriminant equation using the sample statistics of the reference sample sets for which the candidate statistical distribution is the identified candidate statistical distribution.

6. The method of claim 5, wherein the deriving step further comprises:
   calibrating the in-line inspection measurement data in the datasets according to a calibration function between in-line inspection measurements and sampled measurement data.

7. The method of claim 5, further comprising:
   for each dataset, obtaining pipeline descriptors for its associated reference pipeline from which its inline inspection measurement data are acquired;
   wherein the step of deriving a discriminant equation also uses the pipeline descriptors of the reference pipelines for the dataset from which the reference sample set is taken.

8. The method of claim 7, further comprising:
   obtaining pipeline descriptors for the pipeline;
   wherein the applying step also applies the pipeline descriptors to the discriminant function.

9. An evaluation system for evaluating measurements of pipeline wall thicknesses, comprising:
   a memory resource for storing a data library;
   one or more central processing units for executing program instructions; and
   program memory, coupled to the central processing unit, for storing a computer program including program instructions that, when executed by the one or more central processing units, is capable of causing the computer system to perform a sequence of operations for estimating the integrity of a pipeline, the sequence of operations comprising:
      receiving sampled measurement data of pipeline wall thickness loss for the pipeline, the measurement data obtained at a plurality of sample locations along the pipeline;
      calculating sample statistics of the sampled measurement data;
      retrieving a discriminant function from the data library;
      applying the sample statistics to the discriminant function, the discriminant function arranged to identify one of a plurality of candidate statistical distributions for accuracy in estimating an extreme value of pipeline wall thickness loss, each of the plurality of candidate statistical distributions based on wall thickness loss measurements of a corresponding one of a plurality of reference pipelines; and
      evaluating an extreme value quantile of the identified candidate statistical distribution as fit to the sampled measurement data to obtain an estimate of an extreme value of pipeline wall thickness loss for the pipeline.

10. The evaluation system of claim 9, further comprising:
    a network interface for presenting and receiving communication signals to a network accessible to users;
    wherein the memory resource is accessible to the central processing units via the network interface.

11. The evaluation system of claim 9, wherein the operation of receiving sampled measurement data comprises:
accessing the memory resource.

12. The evaluation system of claim 9, wherein the sequence of operations further comprises:
obtaining pipeline descriptors for the pipeline;
and wherein the pipeline descriptors are also applied to the discriminant function in the applying operation.

13. The evaluation system of claim 9, wherein the discriminant function comprises a plurality of linear equations, each associated with a candidate statistical distribution.

14. The evaluation system of claim 9, wherein the sequence of operations further comprises:
retrieving, from the data library, inline inspection measurement datasets for the plurality of reference pipelines; and
deriving the discriminant function from Monte Carlo sampling of the inline inspection measurement datasets.

15. The evaluation system of claim 14, wherein the operation of deriving the discriminant function comprises:
identifying an extreme value of pipeline wall thickness loss in each of the plurality of datasets;
for each of the plurality of datasets, at each of a plurality of sample sizes, randomly sampling each of the datasets one or more times, to derive a plurality of reference sample sets;
for each of the reference sample sets:
calculating one or more sample statistics for the sample set;
evaluating an extreme value quantile using each of the plurality of candidate statistical distributions as fit to the sample set, to obtain an estimate of an extreme value of pipeline wall thickness loss;
comparing the evaluated extreme value quantile from each of the plurality of candidate statistical distributions to the extreme value of pipeline wall thickness loss for the dataset from which the reference sample set is taken; and
then, for each of the datasets, identifying one of the candidate statistical distributions for which the evaluated extreme value quantile is closest to the extreme value of pipeline wall thickness loss for the dataset from which the reference sample set is taken; and
for each of the candidate statistical distributions, deriving a discriminant equation using the sample statistics of the reference sample sets for which the candidate statistical distribution is the identified candidate statistical distribution.

16. The evaluation system of claim 15, wherein the operation of deriving the discriminant function further comprises:
calibrating the in-line inspection measurement data in the datasets according to a calibration function between in-line inspection measurements and sampled measurement data.

17. The evaluation system of claim 15, wherein the sequence of operations further comprises:
for each dataset, retrieving pipeline descriptors for its associated reference pipeline from which its inline inspection measurement data are acquired;
and wherein the operation of deriving a discriminant equation also uses the pipeline descriptors of the reference pipelines for the dataset from which the reference sample set is taken.

18. The evaluation system of claim 17, wherein the sequence of operations further comprises:
obtaining pipeline descriptors for the pipeline;
and wherein the applying operation also applies the pipeline descriptors to the discriminant function.

19. A computer-readable medium storing a computer program that, when executed on a computer system, causes the computer system to perform a sequence of operations for estimating the integrity of a pipeline, the sequence of operations comprising:
receiving sampled measurement data of pipeline wall thickness loss for the pipeline, the measurement data obtained at a plurality of sample locations along the pipeline;
calculating sample statistics of the sampled measurement data;
applying the sample statistics to a discriminant function, the discriminant function arranged to identify one of a plurality of candidate statistical distributions for accuracy in estimating an extreme value of pipeline wall thickness loss, each of the plurality of candidate statistical distributions based on wall thickness loss measurements of a corresponding one of a plurality of reference pipelines; and
evaluating an extreme value quantile of the identified candidate statistical distribution as fit to the sampled measurement data to obtain an estimate of an extreme value of pipeline wall thickness loss for the pipeline.

20. The computer-readable medium of claim 19, wherein the sequence of operations further comprises:
obtaining pipeline descriptors for the pipeline;
and wherein the operation of applying the sample statistics to a discriminant function also applies the pipeline descriptors to the discriminant function.

21. The computer-readable medium of claim 19, wherein the discriminant function comprises a plurality of linear equations, each associated with a candidate statistical distribution.

22. The computer-readable medium of claim 19, wherein the sequence of operations further comprises:
deriving the discriminant function from inline inspection measurement datasets for the plurality of reference pipelines by:
identifying an extreme value of pipeline wall thickness loss in each of the plurality of datasets;
for each of the plurality of datasets, at each of a plurality of sample sizes, randomly sampling each of the datasets one or more times, to derive a plurality of reference sample sets;
for each of the reference sample sets:
calculating one or more sample statistics for the sample set;
evaluating an extreme value quantile using each of the plurality of candidate statistical distributions as fit to the sample set, to obtain an estimate of an extreme value of pipeline wall thickness loss;
comparing the evaluated extreme value quantile from each of the plurality of candidate statistical distributions to the extreme value of pipeline wall thickness loss for the dataset from which the reference sample set is taken; and
then, for each of the datasets, identifying one of the candidate statistical distributions for which the evaluated extreme value quantile is closest to the extreme value of pipeline wall thickness loss for the dataset from which the reference sample set is taken; and
for each of the candidate statistical distributions, deriving a discriminant equation using the sample statistics of the reference sample sets for which the candidate statistical distribution is the identified candidate statistical distribution.

23. The computer-readable medium of claim 22, wherein the operation of deriving the discriminant function further comprises:
calibrating the in-line inspection measurement data in the datasets according to a calibration function between in-line inspection measurements and sampled measurement data.

24. The computer-readable medium of claim 22, wherein the sequence of operations further comprises:
for each dataset, obtaining pipeline descriptors for its associated reference pipeline from which its inline inspection measurement data are acquired; and
obtaining pipeline descriptors for the pipeline;
wherein the step of deriving a discriminant equation also uses the pipeline descriptors of the reference pipelines for the dataset from which the reference sample set is taken;
and wherein the applying step also applies the pipeline descriptors to the discriminant function.

* * * * *